US012653970B2

(12) United States Patent 
Chen et al.

(10) Patent No.: US 12,653,970 B2 
(45) Date of Patent: Jun. 16, 2026

(54) NEBULIZER WITH DETECTING STRUCTURE

(71) Applicant: GALEMED CORPORATION, Yilan County (TW)

(72) Inventors: Po-Chang Chen, Yilan County (TW); Hsin-Chen Wang, Yilan County (TW); Chia-Chin Yang, Yilan County (TW); Hao-Hsiang Chen, Yilan County (TW); Chun-Wei Hsu, Yilan County (TW)

(73) Assignee: GALEMED CORPORATION, Yilan County (TW)

( * ) Notice: Subject to any disclaimer, the term of this patent is extended or adjusted under 35 U.S.C. 154(b) by 1063 days.

(21) Appl. No.: 17/750,256

(22) Filed: May 20, 2022

(65) Prior Publication Data

US 2023/0372640 A1 Nov. 23, 2023

(51) Int. Cl. 
*A61M 11/02* (2006.01)

(52) U.S. Cl. 
CPC ..... *A61M 11/02* (2013.01); *A61M 2205/3334* (2013.01); *A61M 2230/40* (2013.01)

(58) Field of Classification Search 
CPC A61M 11/02; A61M 11/005; A61M 15/0091; A61M 15/0085; A61M 2205/3334; A61M 2230/40; A61M 2016/0024; A61M 2016/003 
See application file for complete search history.

(56) References Cited

U.S. PATENT DOCUMENTS

2010/0132699 A1* 6/2010 Burolla ................. A61M 15/00 
128/200.23

FOREIGN PATENT DOCUMENTS

| CN | 205198624 | U | * | 5/2016 | |
| CN | 106178202 | A | * | 12/2016 | ............ A61M 11/00 |
| CN | 110151528 | A | * | 8/2019 | ............ A61H 33/12 |
| CN | 209316730 | U | * | 8/2019 | |
| CN | 212854269 | U | * | 4/2021 | |
| CN | 218551292 | U | * | 3/2023 | |
| TW | I761074 | B | * | 4/2022 | ........ A61M 15/0085 |
| WO | WO-2011135914 | A1 | * | 11/2011 | ........ A61M 16/0063 |

OTHER PUBLICATIONS

English Translation of TW_1761074_B (Year: 2022).* 
English Translation of CN-205198624-U (Year: 2016).* 
English Translation for CN-110151528-A (Year: 2019).*

* cited by examiner

*Primary Examiner* — Kendra D Carter 
*Assistant Examiner* — Maap Ellabib 
(74) *Attorney, Agent, or Firm* — HDLS IPR SERVICES; Chun-Ming Shih

(57) ABSTRACT

A nebulizer (1) includes a host (10) and a nozzle tube (20). The host includes a main body (11), a control module (12) and a sensor (13). The nozzle tube (20) includes a tube (21), a nozzle (22) and a detecting structure (23). The tube (21) includes a chamber (210). The nozzle (22) is arranged on one side of the tube (21) and communicates with the chamber (210). The detecting structure (23) includes a shutter (231) and a swinging member (232) connected with the shutter (231). The shutter (231) is disposed corresponding to the position of the sensor (13). The air blown from the nozzle (22) flows into the tube (21) and blows the swinging member (232) to drive the shutter (231) to activate the sensor (13).

8 Claims, 8 Drawing Sheets

1

22

21

20

23

11

10

20

1

22

21

212

23

232

231

20

11

10

NEBULIZER WITH DETECTING STRUCTURE

BACKGROUND OF THE DISCLOSURE

Technical Field

The technical field relates to a nebulizer, and more particularly relates to a nebulizer with a detecting structure.

Description of Related Art

A nebulizer is a medical device that administers medicine through the respiratory system. The nebulizer atomizes the liquid medicine into tiny liquid droplets with a certain particle size. The atomized medicine is administered into the patient's circulatory system by the nasal and oral administration through inhalation and respirations to accomplish treatment.

However, when using existing nebulizers, most of the nebulizers continuously atomize the liquid medicine without taking a patient's respiratory rate into account during the atomizing process of the liquid medicine, and the nebulizers continuously administer the atomized medicine while the user exhales, and that decreases the effect of administering medication and may cause discomfort to the user.

In view of the above drawbacks, the inventor proposes this disclosure based on his expert knowledge and elaborate researches in order to solve the problems of related art.

SUMMARY OF THE DISCLOSURE

One object of this disclosure is to provide a nebulizer with the detecting structure disposed in the nozzle tube for detecting the user's exhalation. Therefore, the nebulizer stops atomization of the liquid medicine during the user's exhalation to avoid wasting the liquid medicine, and the effect of administering medication may be improved.

In the embodiment of this disclosure, a nebulizer with a detecting structure includes a host and a nozzle tube. The host includes a main body, a control module disposed in the main body and a sensor electrically connected with the control module. The nozzle tube includes a tube, a nozzle and a detecting structure disposed in the tube. The tube includes a chamber. The nozzle is arranged on one side of the tube and communicates with the chamber. The detecting structure includes a shutter and a swinging member connected with the shutter. The shutter is disposed corresponding to the position of the sensor. The air blown from the nozzle flows into the tube and blows the swinging member to drive the shutter to activate the sensor.

In comparison with the related art, the nebulizer in this disclosure includes the detecting structure disposed in the nozzle tube to detect the user's exhalation. When the user exhales, the air blown from the nozzle flows into the tube and blows the swinging member to drive the shutter to activate the sensor. Furthermore, the sensing signal sent from the sensor is transmitted to the control module to achieve the purpose of detecting the user's exhalation. Therefore, the nebulizer stops atomizing the liquid medicine to avoid wasting the liquid medicine and improves the effect of administering medication.

BRIEF DESCRIPTION OF THE DRAWINGS

The features of the disclosure believed to be novel are set forth with particularity in the appended claims. The disclosure itself, however, may be best understood by reference to the following detailed description of the disclosure, which describes a number of exemplary embodiments of the disclosure, taken in conjunction with the accompanying drawings, in which:

DETAILED DESCRIPTION

The technical contents of this disclosure will become apparent with the detailed description of embodiments accompanied with the illustration of related drawings as follows. It is intended that the embodiments and drawings disclosed herein are to be considered illustrative rather than restrictive.

Figure 1:
FIG. 1 is a perspective schematic view of the nebulizer with a detecting structure in this disclosure.
Figure 2:
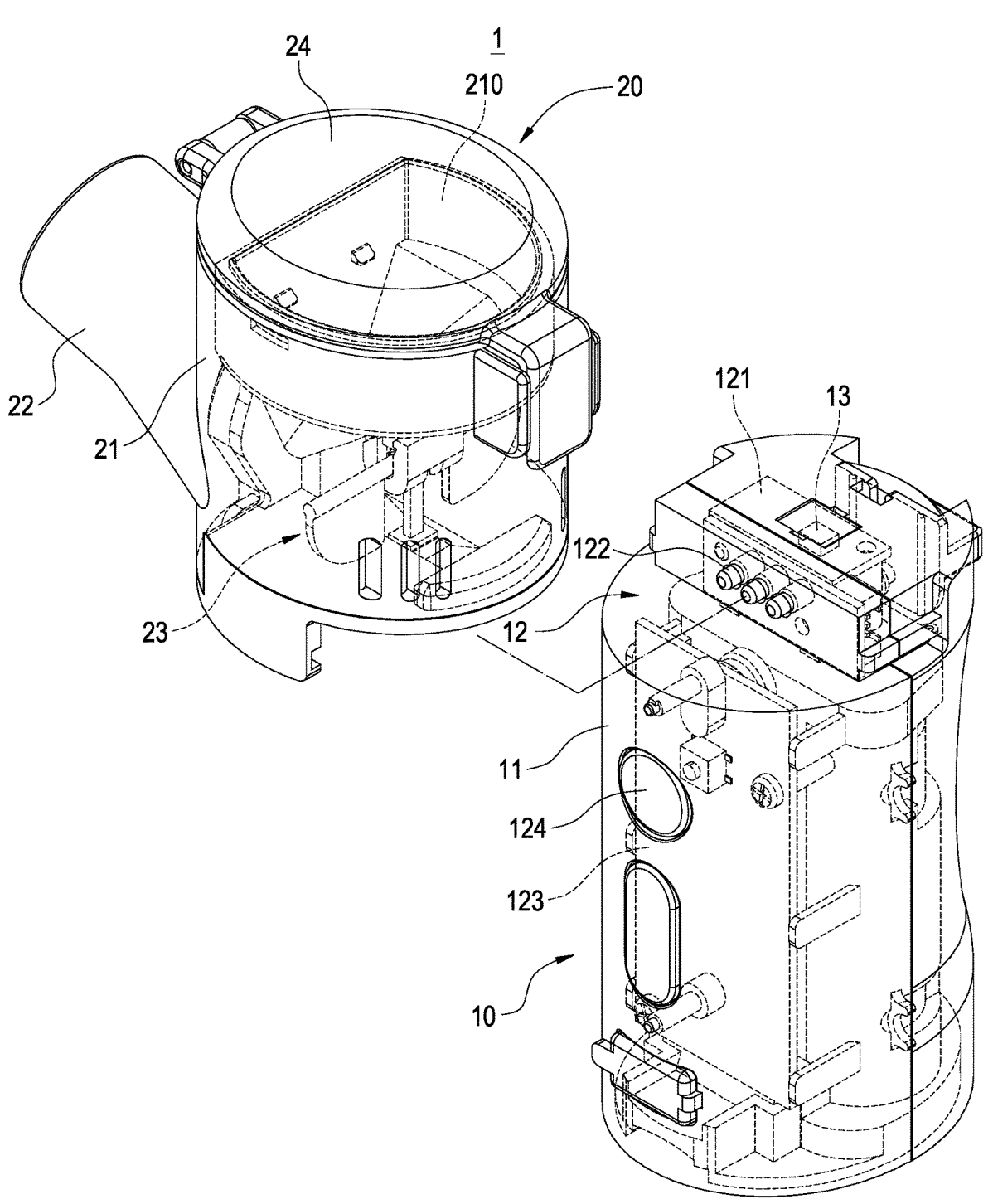
FIG. 2 is a perspective exploded view of the nebulizer with a detecting structure in this disclosure.

Please refer to FIG. 1 and FIG. 2, which depict a perspective schematic view and a perspective exploded view of the nebulizer with a detecting structure in this disclosure. The nebulizer 1 with a detecting structure in this disclosure includes a host 10 and a nozzle tube 20. The nozzle tube 20 is combined on the host 10. The nozzle tube 20 is used to accommodate and atomize the liquid medicine to provide the aerosolized liquid medicine for the user through inhalation. It should be noted that a detecting structure is disposed in nozzle tube 20 for detecting the user's exhalation. Thus, the nebulizer may stop atomizing the liquid medication during the user's exhalation to avoid wasting liquid medicine and improve the effect of administering medication.

The host 10 includes a main body 11, a control module 12 disposed in the main body 11 and a sensor 13 electrically connected with the control module 12. In this embodiment, the control module 12 includes a sensing circuit board 121 and a plurality of conductive terminals 122. The sensor 13 is arranged on the sensing circuit board 121 and electrically connected to the conductive terminals 122. Furthermore, the control module 12 further includes a controlling circuit board 123 and a plurality of buttons 124. The controlling circuit board 123 is electrically connected to the plurality of buttons 124 and the sensing circuit board 121.

The nozzle tube 20 includes a tube 21, a nozzle 22 and a detecting structure 23 disposed in the tube 21. The tube 21 includes a chamber 210 for accommodating the liquid medicinal. In this embodiment, the nozzle tube 20 further includes a top cover 24, and the top cover 24 is movably combined with the tube 21 and covers the chamber 210. In some embodiments, the user may open the top cover 24 and fill the liquid medicine into the chamber 210 for atomizing. Then, the user may inhale the atomized liquid medicine in the chamber 210 from the nozzle 22. The structure of the nozzle tube 20 is described in more detail as follows.

Figure 3:
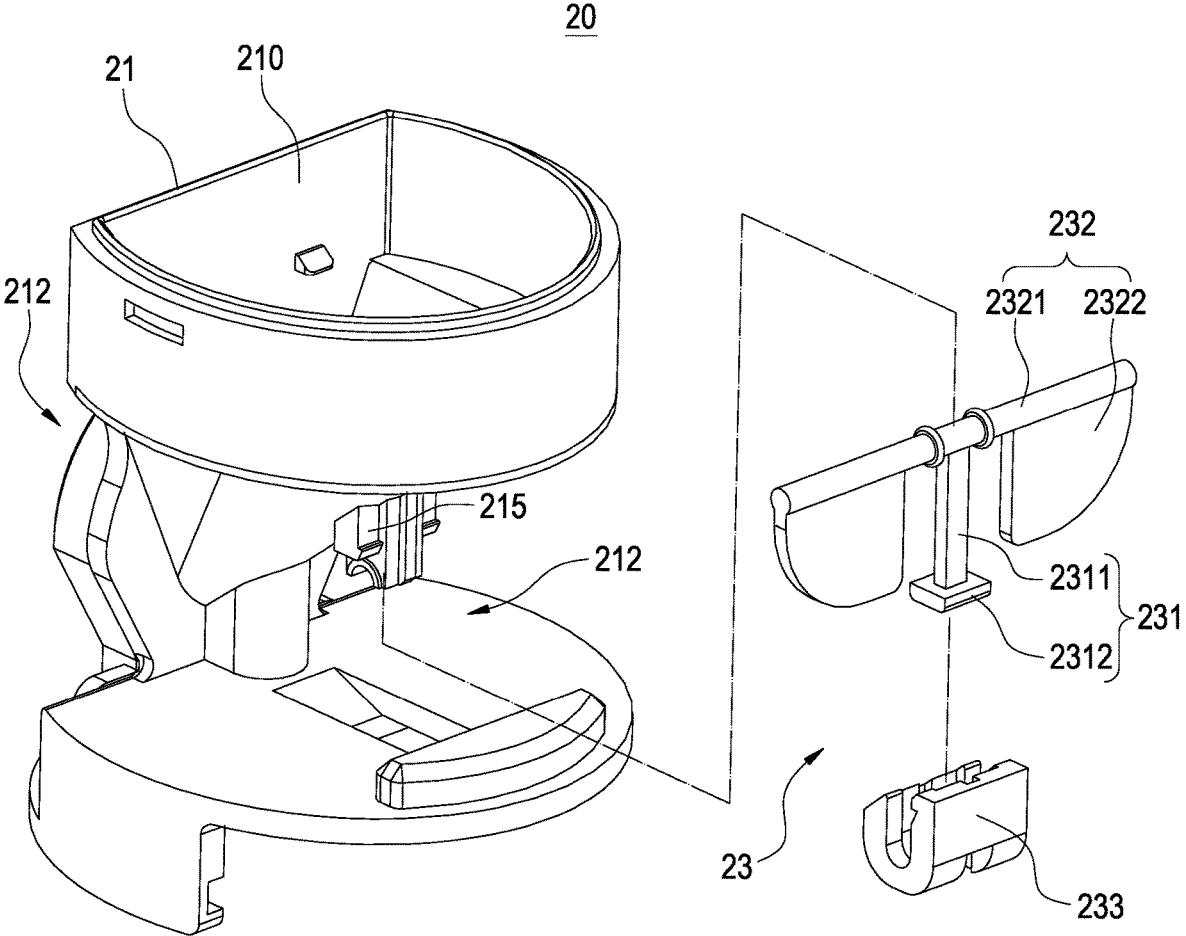
FIG. 3 is a perspective exploded view of the nozzle tube in this disclosure.
Figure 4:
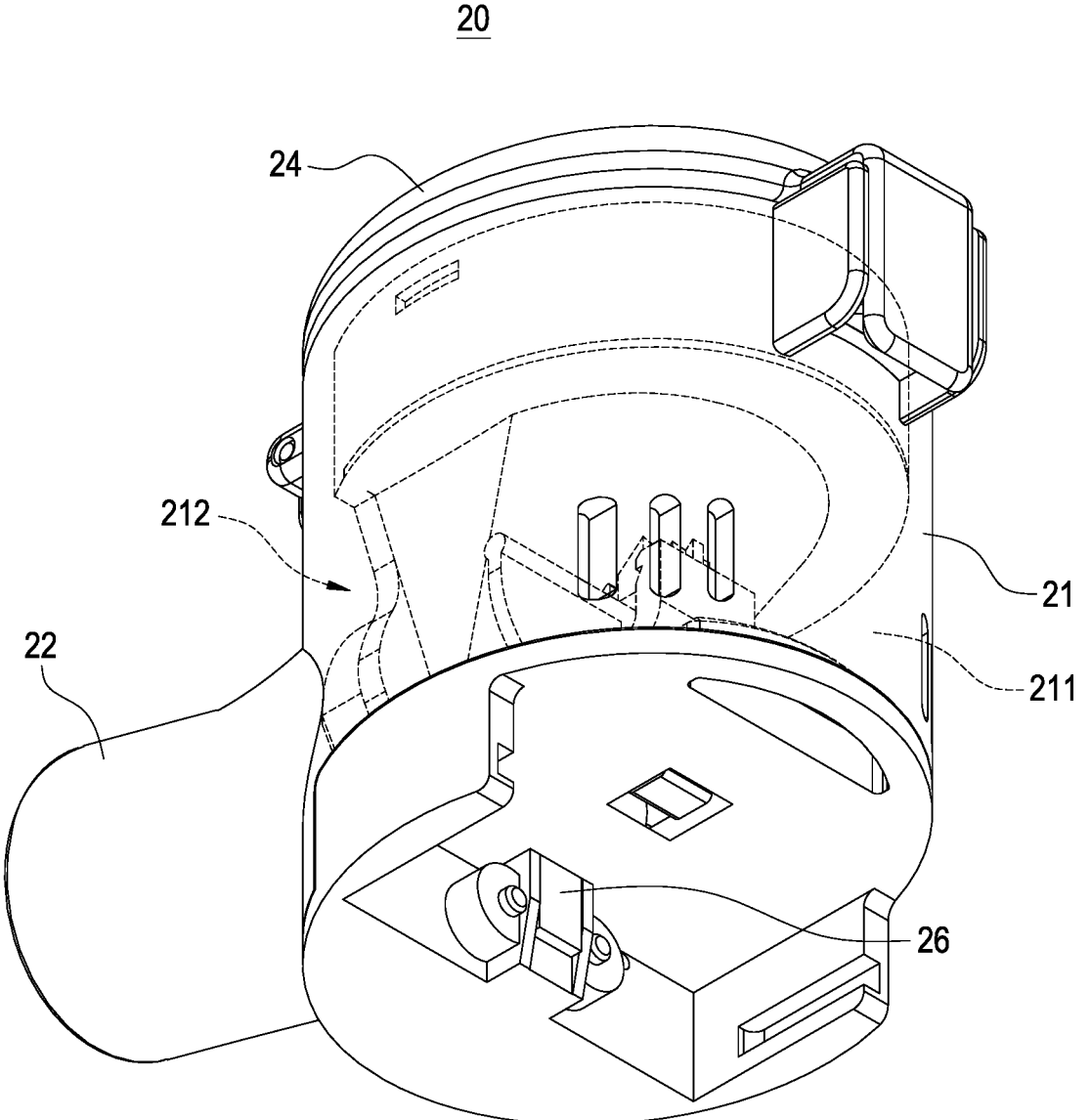
FIG. 4 is a perspective schematic view of the nozzle tube in this disclosure.
Figure 5:
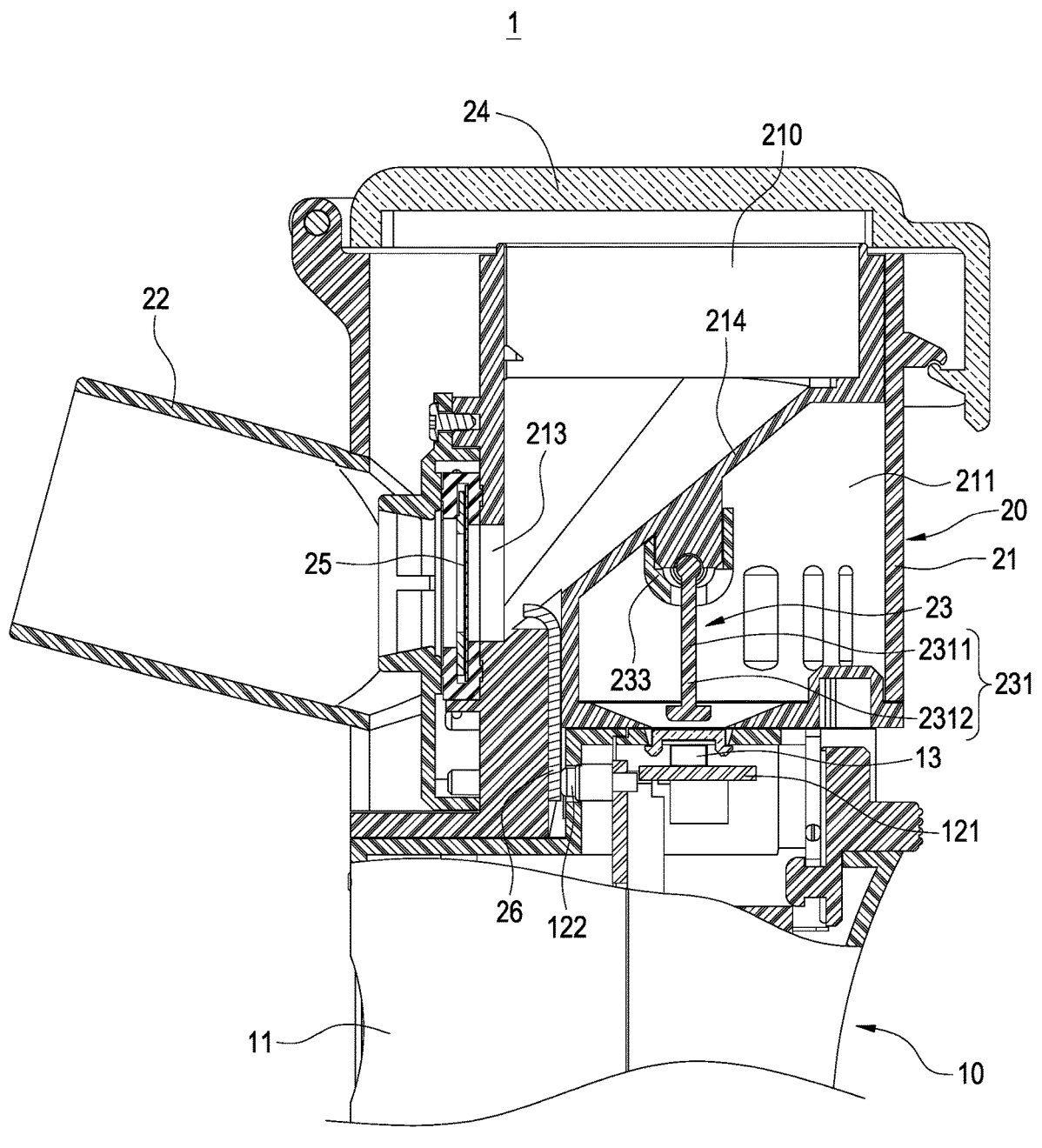
FIG. 5 is a cross sectional view of the nozzle tube in this disclosure.

Please further refer to FIG. 3 to FIG. 5, which depict a perspective exploded view, a perspective schematic view and a cross sectional view of the nozzle tube in this disclosure. As shown in FIG. 3, the tube 21 includes a chamber 210, an exhaust chamber 211, an air passage 212 and a liquid medicine releasing hole 213. The detecting structure 23 is arranged in the exhaust chamber 211. The nozzle 22 is arranged on one side of the tube 21 and communicates with the chamber 210. The nozzle 22 communicates with the exhaust chamber 211 through the air passage 212, and the nozzle 22 communicates with the chamber 210 through the liquid medicine releasing hole 213. Additionally, the tube 21 includes a liquid medicine discharging plate 214 disposed on the bottom side of the chamber 210, and the liquid medicine discharging plate 214 is aligned with edge of the liquid medicine releasing hole 213. Accordingly, the atomized liquid medicine in the chamber 210 flows to the liquid medicine releasing hole 213 and enters the nozzle 22 by the guiding of the liquid medicine discharging plate 214.

In this embodiment, the nozzle tube 20 further includes an atomizing sheet 25. The atomizing sheet 25 is arranged on one side of the liquid medicine releasing hole 213 to filter objects such as impurities flowing into the chamber 210 from the nozzle 22 when the user exhales. In addition, the atomizing sheet 25 also has the functions of vibrating atomization and preventing the liquid medicinal from outflowing.

Moreover, the detecting structure 23 includes a shutter 231, a swinging member 232 and a positioning seat 233 both connected with the shutter 231. The shutter 231 is disposed corresponding to the position of the sensor 13. The shutter 231 includes an extension arm 2311 and a shielding plate 2312. The positioning seat 233 is combined on the tube 21. Moreover, the swinging member 232 includes a rotating shaft 2321 and at least one blade 2322 connected to the rotating shaft 2321. The rotating shaft 2321 is rotatably disposed on the positioning seat 233, and the at least one blade 2322 protrudes from the positioning seat 233. Additionally, one end of the extension arm 2311 is connected to the rotating shaft 2321, and the other end of the extension arm 2311 is connected to the shielding plate 2312 and protrudes from the positioning seat 233 to be positioned above the sensor 13.

It should be noted that the blade 2322 is a thin sheet made of a soft material, and the blade 2322 is blown by air to rotate and swing around the rotating shaft 2321 as the center point.

Specifically, the tube 21 includes a pair of hooks 215 disposed on the liquid medicine discharging plate 214 and located outside the chamber 210. The positioning seat 233 is combined in the exhaust chamber 211 through the pair of hooks 215.

It is worth noticing that the nozzle tube 20 further includes a conductive elastic sheet 26. The conductive elastic sheet 26 is arranged on the bottom of the tube 21. Furthermore, when the host 10 is assembled on the bottom side of the nozzle tube 20, the conductive terminals 122 of the host 10 are electrically connected to the conductive elastic pieces 26.

Figure 6:
FIG. 6 is a schematic view illustrating operation of the nebulizer in exhalation in this disclosure.
Figure 7:
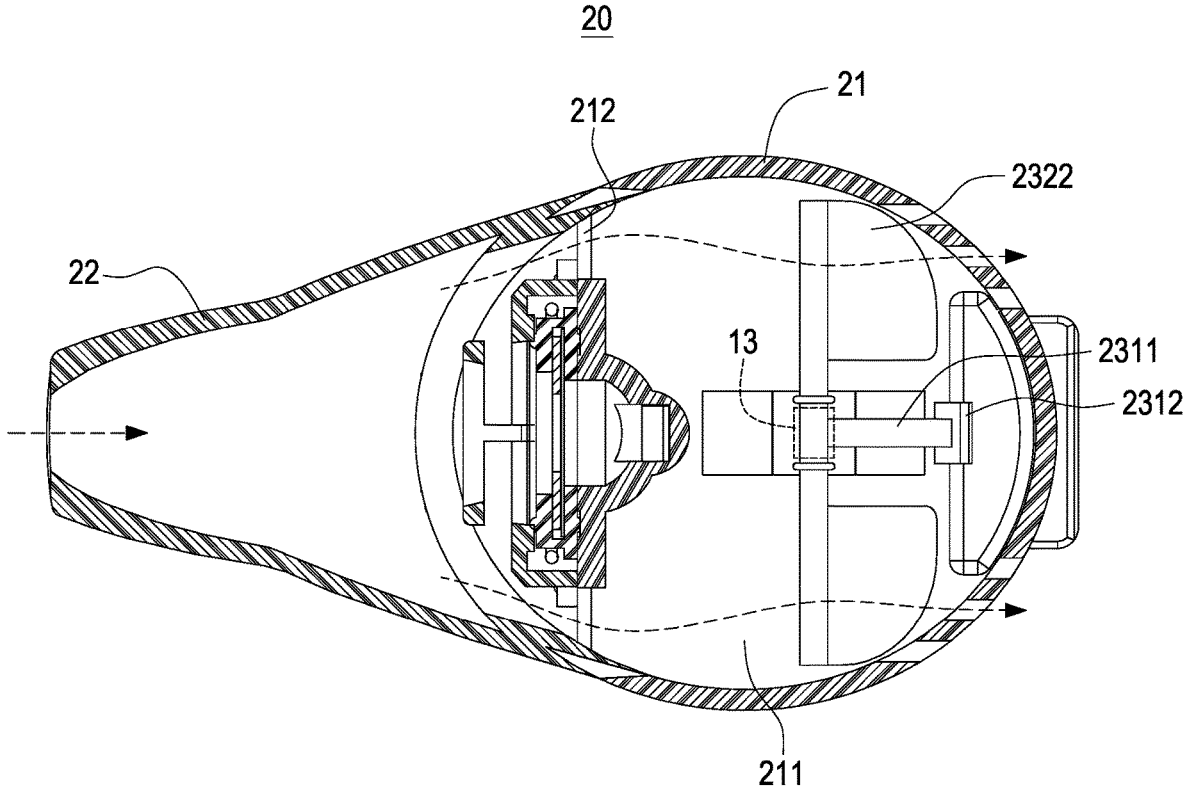
FIG. 7 is a schematic view of the air flow path of the nebulizer in exhalation in this disclosure.
Figure 8:
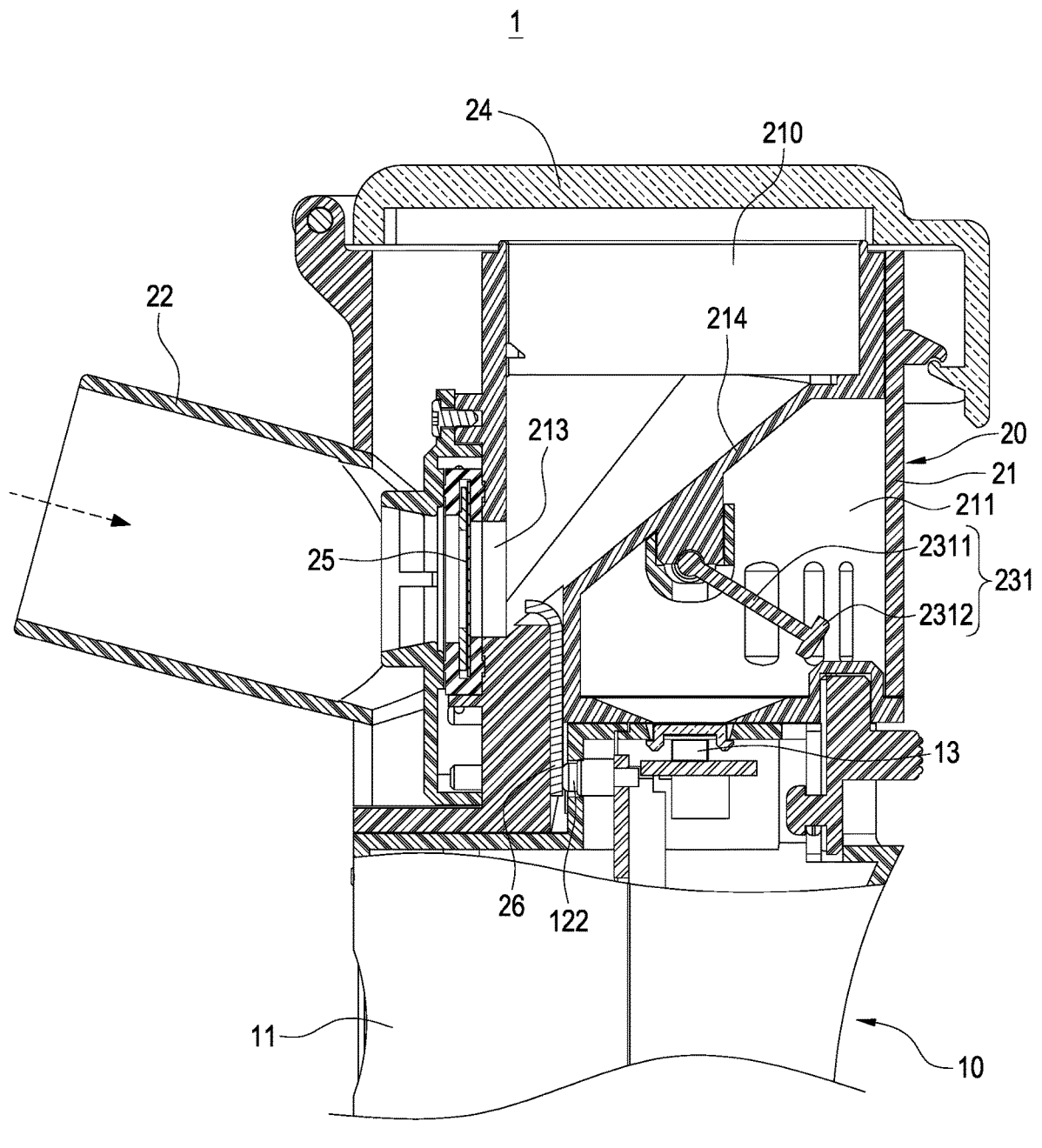
FIG. 8 is a cross sectional view of the nebulizer in exhalation in this disclosure.

Please further refer to FIG. 6 to FIG. 8, which depict a schematic view illustrating operation of the nebulizer in exhalation in this disclosure, a schematic view of the air flow path of the nebulizer in exhalation, and a cross sectional view of the nebulizer in exhalation in this disclosure. As shown in the figures, when the user exhales, the air blown from the nozzle 22 flows into the tube 21 and blows the swinging member 232 to drive the shutter 231 to activate the sensor 13. In more detail, when the user exhales, the air blown from the nozzle 22 flows into the exhaust chamber 211 from the air passages 212 on both sides of the tube 21 and blows the swinging member 232. Then, the blade 2322 swings around the rotating shaft 2321 and drives the shutter 231 to rotate. Additionally, the shielding plate 2312 of the shutter 231 leaves the sensing range of the sensor 13 to activate the sensor 13 and send out a sensing signal.

It should be noted that the sensing signal sent from the sensor 13 is transmitted to the sensing circuit board 121, and further the signal is transmitted to the control module 12 for detecting the user's exhalation. Accordingly, when the sensor 13 detects the user's exhalation, the control module 12 stops atomizing the liquid medicinal. Therefore, waste of liquid medicinal is avoided and the effect of administering medication is improved.

While this disclosure has been described by means of specific embodiments, numerous modifications and variations could be made thereto by those skilled in the art without departing from the scope and spirit of this disclosure set forth in the claims.

What is claimed is:

1. A nebulizer (1), comprising: a host (10), comprising a main body (11), a control module (12) disposed in the main body (11) and a sensor (13) electrically connected with the control module (12); and a nozzle tube (20), comprising a tube (21), a nozzle (22) and a detecting structure (23) disposed in the tube (21); wherein the tube (21) comprises a chamber (210), the nozzle (22) is arranged on one side of the tube (21) and communicates with the chamber (210); the detecting structure (23) comprises a shutter (231) and a swinging member (232) connected with the shutter (231), and the shutter (231) is disposed corresponding to a position of the sensor (13); and air blown from the nozzle (22) flows into the tube (21) to blow the swinging member (232) to drive the shutter (231) to activate the sensor (13); wherein the tube (21) comprises an exhaust chamber (211) and an air passage (212); and the detecting structure (23) is arranged in the exhaust chamber (211), and the nozzle (22) communicates with the exhaust chamber (211) through the air passage (212); wherein the tube (21) comprises a liquid medicine releasing hole (213), and the nozzle (22) communicates with the chamber (210) through the liquid medicine releasing hole (213); the tube (21) comprises a liquid medicine discharging plate (214) disposed on a bottom side of the chamber (210) and aligned with an edge of the liquid medicine releasing hole (213) wherein the detecting structure (23) further comprises a positioning seat (233) combined on the tube (21); the swinging member (232) comprises a rotating shaft (2321) and at least one blade (2322) connected to the rotating shaft (2321); the rotating shaft (2321) is rotatably disposed on the positioning seat (233), and the at least one blade (2322) protrudes from the positioning seat (233).

2. The nebulizer (1) according to claim 1, wherein the control module (12) comprises a sensing circuit board (121) and a plurality of conductive terminals (122), and the sensor (13) is arranged on the sensing circuit board (121) and electrically connected to the plurality of conductive terminals (122).

3. The nebulizer (1) according to claim 2, wherein the control module (12) further comprises a controlling circuit board (123) and a plurality of buttons (124), and the controlling circuit board (123) is electrically connected to the plurality of buttons (124) and the sensing circuit board (121).

4. The nebulizer (1) according to claim 1, wherein the nozzle tube (20) further comprises a top cover (24), and the top cover (24) is movably combined with the tube (21) and covers the chamber (210).

5. The nebulizer (1) according to claim 1, wherein the nozzle tube (20) further comprises an atomizing sheet (25) arranged on one side of the liquid medicine releasing hole (213).

6. The nebulizer (1) according to claim 1, wherein the shutter (231) comprises an extension arm (2311) and a shielding plate (2312); and one end of the extension arm (2311) is connected to the rotating shaft (2321), and another end of the extension arm (2311) is connected to the shielding plate (2312) and protrudes from the positioning seat (233) to be positioned above the sensor (13).

7. The nebulizer (1) according to claim 1, wherein the tube (21) comprises a pair of hooks (215) disposed on the liquid medicine discharging plate (214) and located outside the chamber (210), and the positioning seat (233) is combined in the exhaust chamber (211) through the pair of hooks (215).

8. The nebulizer (1) according to claim 1, wherein the at least one blade (2322) is a thin sheet made of a soft material.

* * * * *